United States Patent [19]

Simpson et al.

[11] Patent Number: 5,571,130
[45] Date of Patent: Nov. 5, 1996

[54] ATHERECTOMY AND PROSTECTOMY SYSTEM

[75] Inventors: John B. Simpson; Hanson S. Gifford, both of Woodside, Calif.

[73] Assignee: Advanced Cardiovascular Systems, Inc., Santa Clara, Calif.

[21] Appl. No.: 317,809

[22] Filed: Oct. 4, 1994

[51] Int. Cl.$^6$ ............................................. A61B 17/32
[52] U.S. Cl. ........................... 606/171; 606/159; 606/170
[58] Field of Search ................................ 606/159, 170, 606/180, 171

[56] References Cited

U.S. PATENT DOCUMENTS

| | | | |
|---|---|---|---|
| 68,647 | 9/1867 | Palmer | 606/159 |
| 1,663,761 | 3/1928 | Johnson | 606/159 |
| 4,020,847 | 5/1977 | Clark, III | 606/159 |
| 4,627,436 | 12/1986 | Leckrone | 606/7 |
| 4,669,469 | 6/1987 | Gifford, III et al. | 606/159 |
| 4,685,458 | 8/1987 | Leckrone | 606/7 |
| 4,747,405 | 5/1988 | Leckrone | 606/7 |
| 4,819,634 | 4/1989 | Shiber | 606/159 |
| 4,842,579 | 6/1989 | Shiber | 604/22 |
| 4,883,458 | 11/1989 | Shiber | 604/22 |
| 4,886,490 | 12/1989 | Shiber | 604/22 |
| 4,894,051 | 1/1990 | Shiber | 604/22 |
| 4,917,097 | 4/1990 | Proudian et al. | 128/662.06 |
| 4,919,133 | 4/1990 | Chiang | 606/159 |
| 4,966,604 | 10/1990 | Reiss | 606/159 |
| 4,979,951 | 12/1990 | Simpson | 606/159 |
| 4,986,807 | 1/1991 | Farr | 604/22 |
| 5,171,255 | 12/1992 | Rydell | 606/170 |
| 5,242,460 | 9/1993 | Klein et al. | 606/159 |
| 5,250,060 | 10/1993 | Carbo et al. | 606/159 |
| 5,368,603 | 11/1994 | Halliburton | 606/159 |
| 5,431,673 | 7/1995 | Summers et al. | 606/170 |

*Primary Examiner*—Michael Powell Buiz
*Assistant Examiner*—Patrick W. Rasche
*Attorney, Agent, or Firm*—Fulwider Patton Lee & Utecht

[57] ABSTRACT

An improved system for removing atheromas in a blood vessel or ablating tissue of a gland that includes a catheter with a housing containing a cutout or window at its distal end, and an excising or ablating element disposed therein. The excising or ablating element is characterized by at least one cutting blade with a relatively straight cutting edge, that has a length approximately the same as the length of the cutout when measured along a longitudinal axis of the system. In operation, the cutout is positioned at the site at which treatment is to be rendered using a guiding element. Each cutting blade then is caused to reciprocate by a driving element and to move back and forth by an actuating element to alternately cover and uncover the cutout. In the process of reciprocating and traversing the cutout the cutting blade or cutting blades remove the target atheroma or tissue.

11 Claims, 6 Drawing Sheets

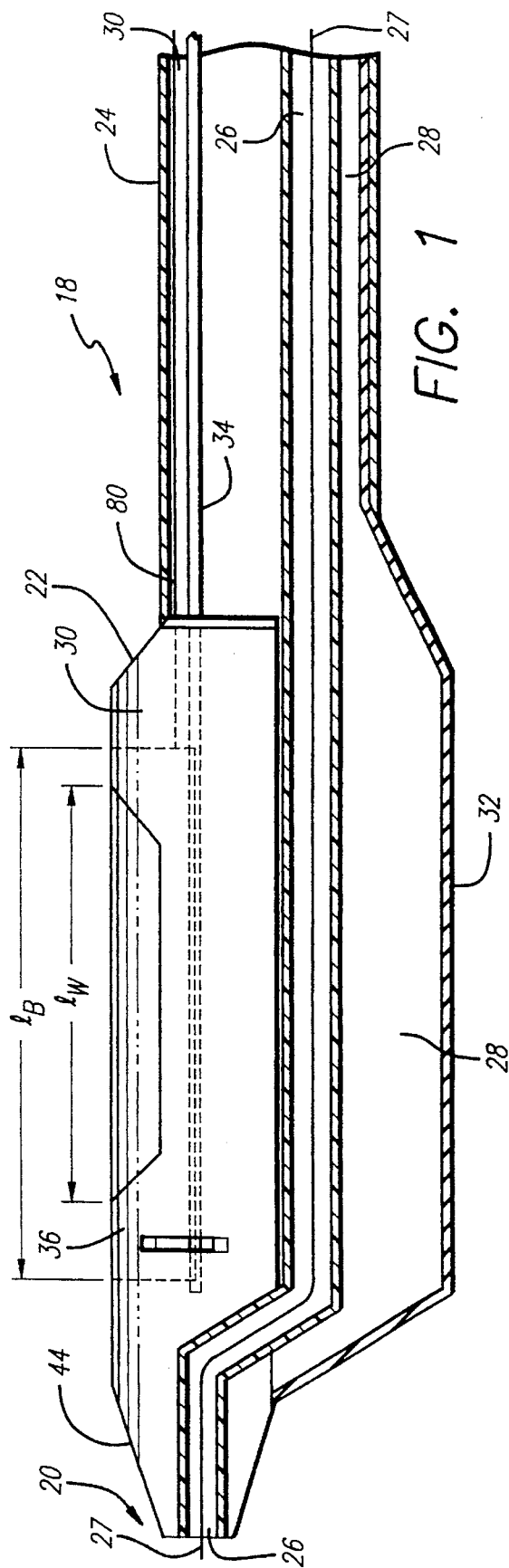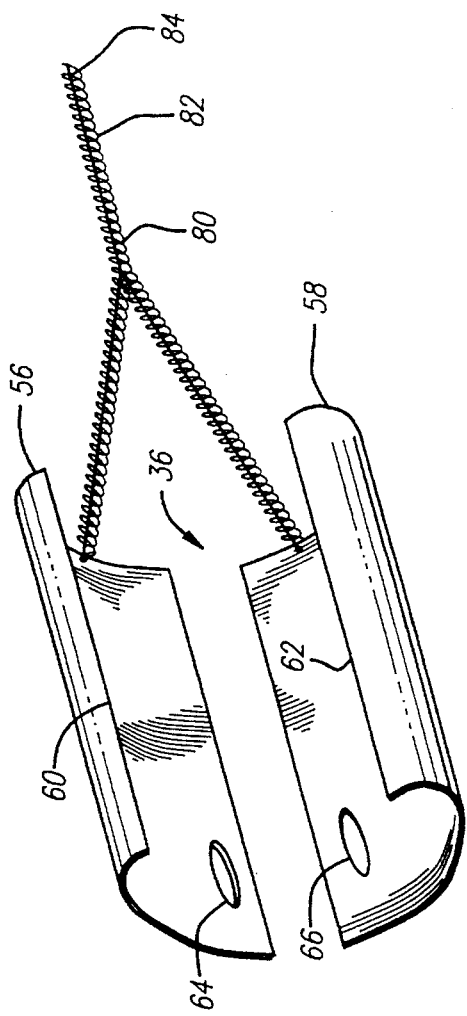

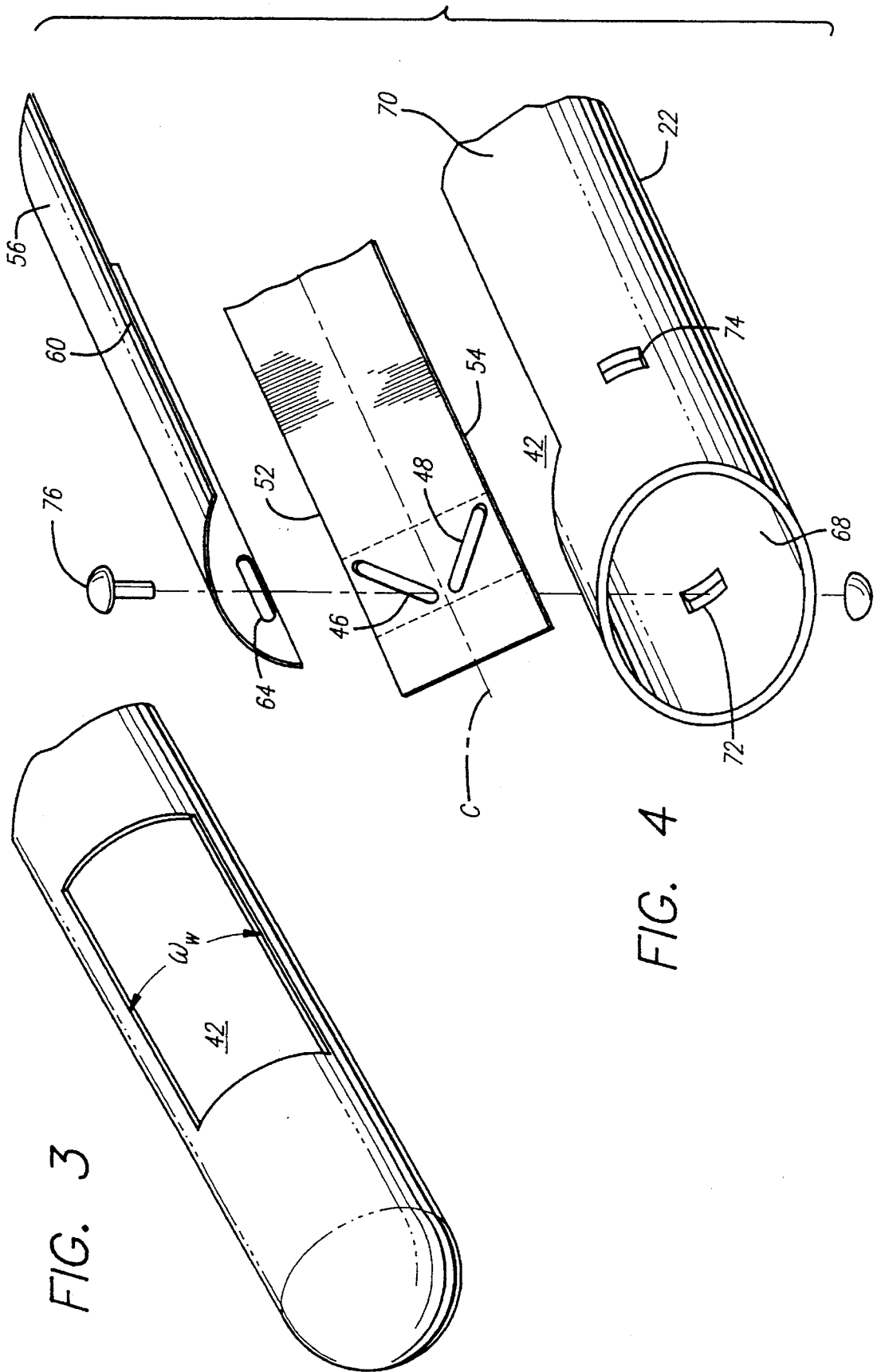

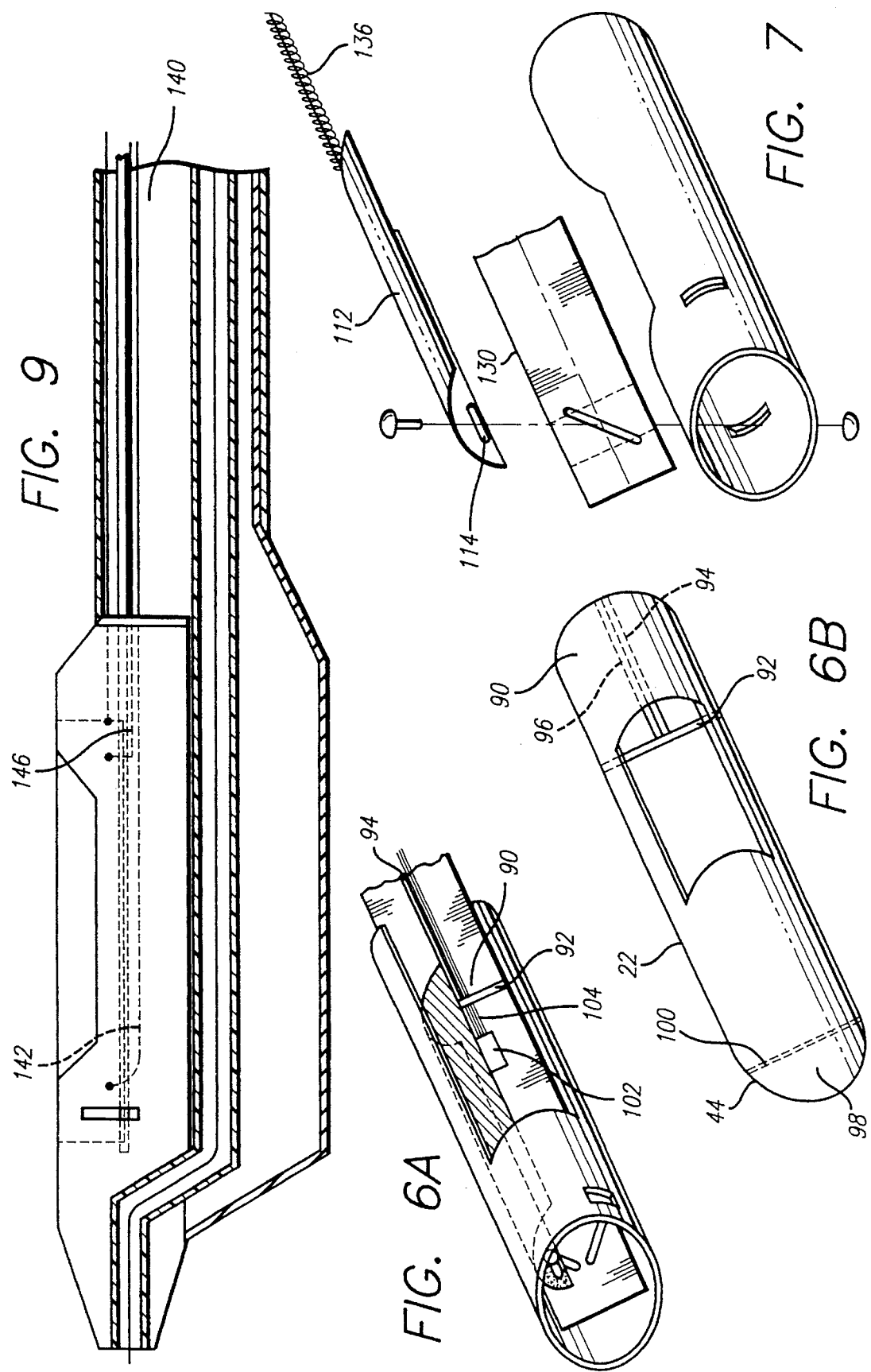

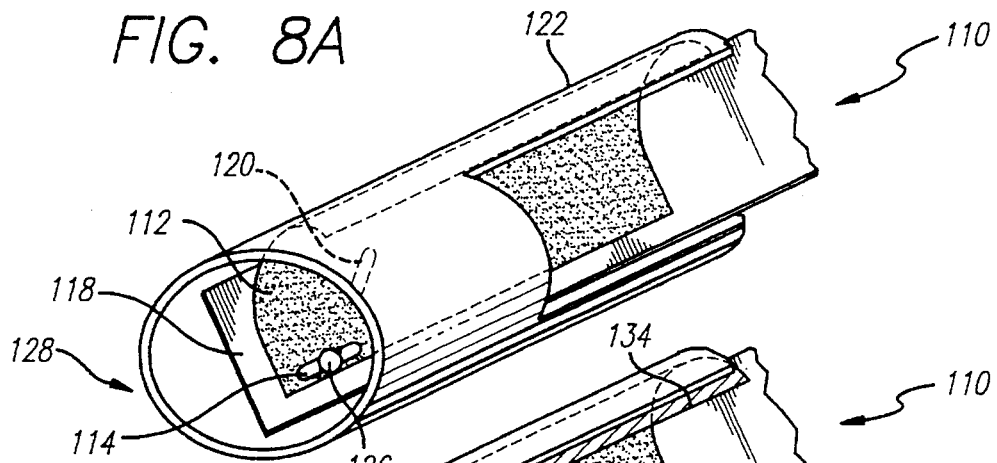
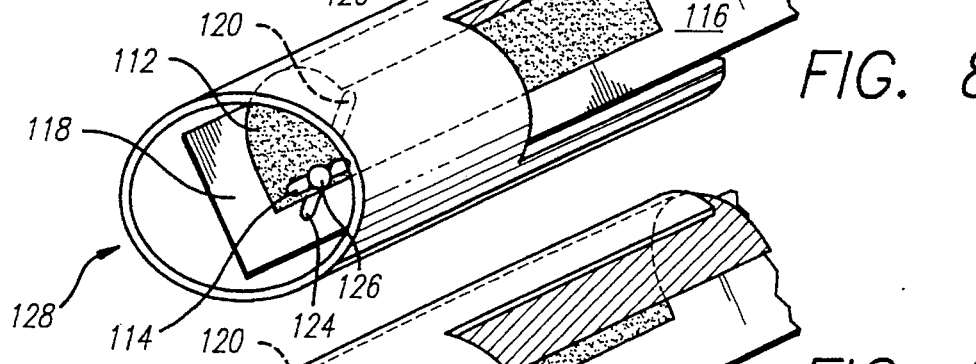
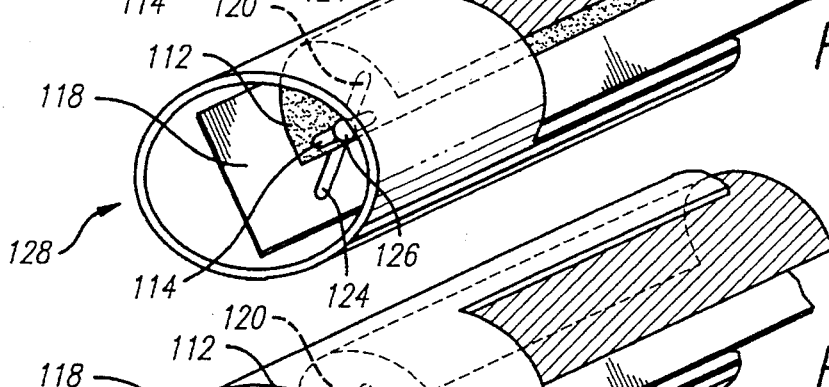
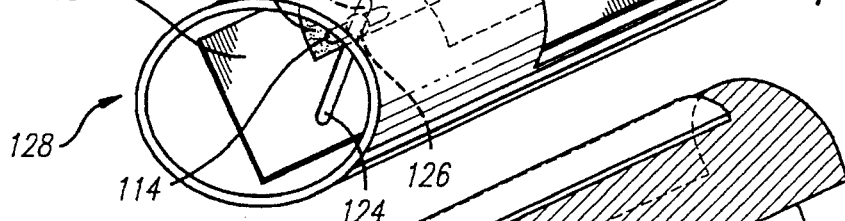
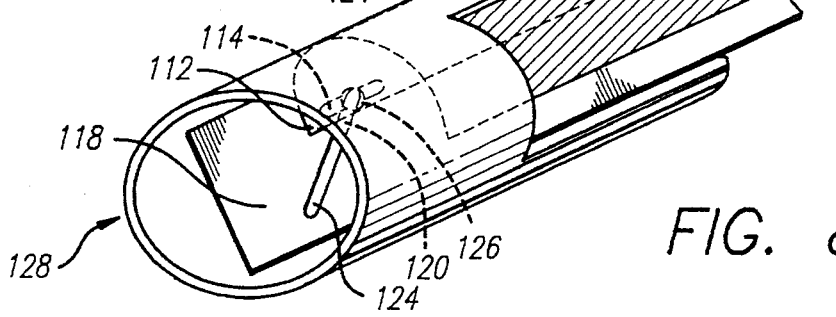

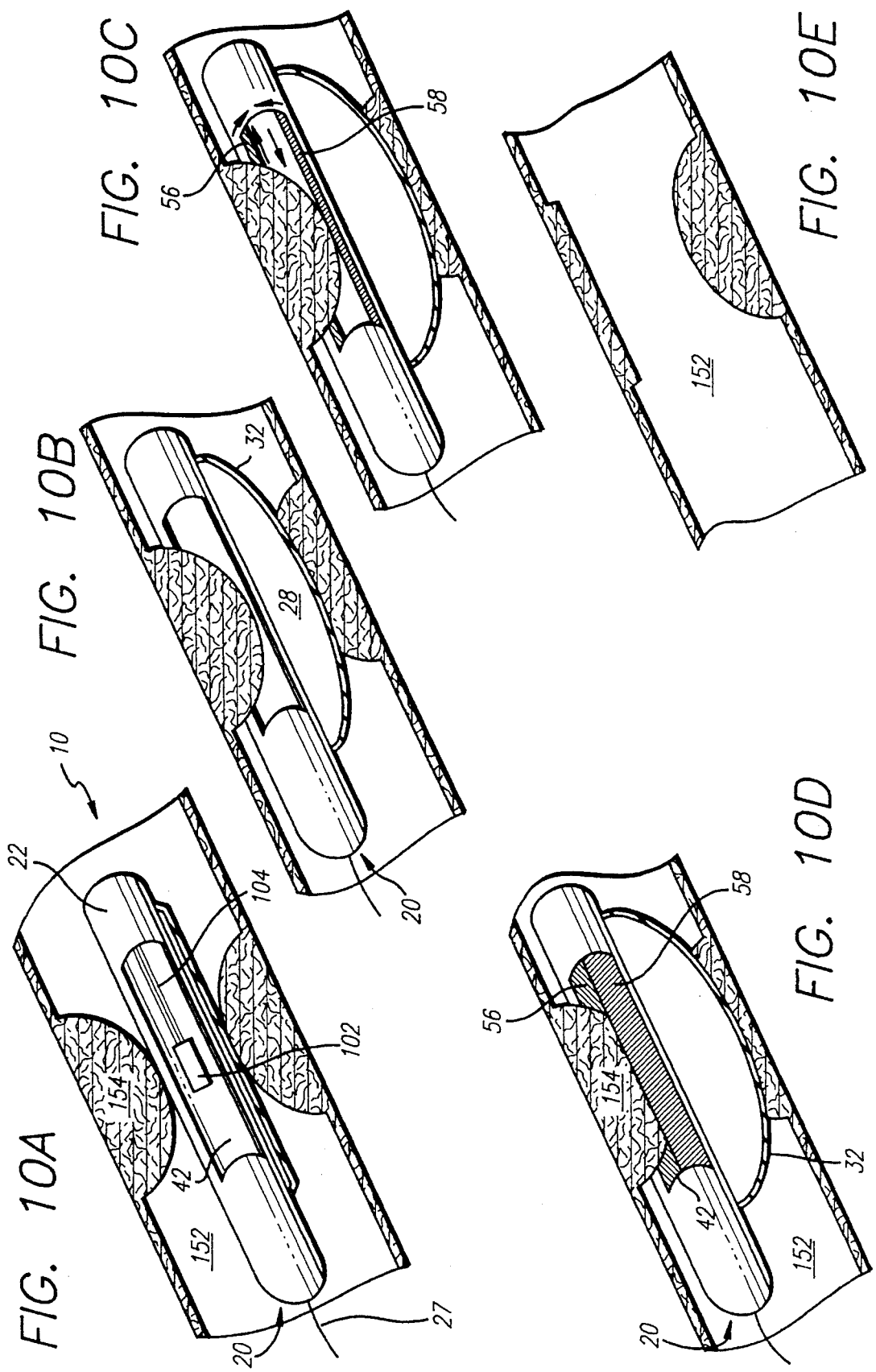

ATHERECTOMY AND PROSTECTOMY SYSTEM

BACKGROUND OF THE INVENTION

The invention relates generally to an improved apparatus and method for excising atheromas from the lumina of blood vessels and diseased tissue from other interstitial body spaces. More particularly, the invention relates to new and improved catheter-borne atherectomy systems for removing diseased tissue from the lumina of human arteries and which can be adapted to ablate glandular tissue, for instance, in a prostectomy.

Fatty deposits accumulated in the coronary or peripheral arteries of a human patient are known to threaten health. Once such a condition has been diagnosed, a physician has available several different courses of treatment. One of these is bypass surgery, in which a portion of the affected vessel is replaced with a portion of a healthier vessel. This method typically is viewed as a last resort because it involves open surgery which inherently presents more risk to a patient than other available methods.

Another treatment method is angioplasty, in which a balloon catheter is inserted into the body and the balloon is positioned where the disease occurs, referred to variously as the stenosis, atheroma, and plaque. The balloon then is inflated under pressure to press the stenosis against the walls of the vessel in order to expand the lumen and thereby increase blood flow.

An atherectomy is a third method for treating stenosed portions of an artery or other vessel. This procedure involves the resection of the atheroma from the affected vessel with a cutting device which is carried to the location at which treatment is to be rendered by a catheter.

Prior art atherectomy catheter systems include a generally circular cylindrical housing bearing a cutting blade, the housing being mounted on a balloon catheter. The cutting surface of the blade has a curvature which approximates the curvature of the housing. The housing has a cutout or window near its distal end, and a guidewire is used to position the catheter and the housing window at the affected site in the blood vessel. The balloon is inflated to push the window up against the plaque and the cutting blade is pushed into the window. The blade slices off the atheroma as it slowly traverses the length of the window, and the cut material falls into the window. Some of these atherectomy systems include an element to push the cut material into the nose of the housing and to retain it there until after the catheter system is removed from the patient, to prevent the tissue debris from entering the blood stream and possibly causing complications.

In such systems, the cutting blade commonly is cylindrically-shaped, such that the curvature of the blade roughly approximates but may not match the curvature of the arterial wall, because the curvature of the wall most often is ellipsoidal. Thus, it can be difficult to cut all of the material targeted for resection on a single pass of the blade. The efficiency with which the procedure can be accomplished is adversely impacted by the need to resort to multiple passes of the blade and the attendant need to proceed more slowly as deeper and deeper cuts are made to avoid resecting healthy tissue along with the plaque. Further, care must be taken when performing an atherectomy with a system incorporating a blade that cuts as it advances along the longitudinal axis of the artery, as this type of cutting action can have a tendency to cut more and more deeply into the luminal surface as the blade advances. This can result in an uneven luminal surface which might lead to less than optimum blood flow or might increase the likelihood that stenosis will reoccur at the site treated by the atherectomy. When such prior art atherectomy systems are used to perform prostatectomies, the need for precision also can make it time-consuming to avoid inadvertently cutting or burning non-prostatic tissue surrounding the prostate gland.

Atherectomy systems also can be adapted for use in prostatectomies in which an enlarged or diseased prostate gland is removed. In such a procedure, the atherectomy system is enhanced with a heating element and is used in transurethral resection of the prostate, the catheter usually being inserted through a channel of a cystoscope to deliver the excising or ablating element and associated heating element, which are used to accomplish the resection by a combination of cutting action and of selectively increasing the temperature of the excising or ablating element to facilitate ablation of the glandular tissue. As is the case in the atherectomy application, catheter-borne systems can lead to inefficiency when used in prostatectomies, due to the time-consuming attention to precision that is mandated because of the shape and cutting path of the blades. Care must be exercised so that only the target tissue is ablated.

What has been needed then, and what has heretofore been unavailable, is a system that can deliver a cutting mechanism to a vessel or organ designated for treatment via a device such as a catheter, which avoids resort to open surgery, and that is configured to allow precise cutting action without compromising the overall efficiency with which the procedure can be accomplished.

SUMMARY OF THE INVENTION

Briefly, and in general terms, the present invention addresses the need for a system for removing an atheroma or ablating glandular tissue which can be conveniently deployed by a catheter and which can precisely deliver a sharp cutting action to the diseased portion of the vessel wall or to the gland with optimal efficiency.

A system in accordance with the present invention includes a housing that rests on the distal portion of a catheter; that is, the portion of the catheter which will be positioned at the treatment site during an atherectomy or prostectomy. The catheter is provided with a guiding element or with a dedicated guide lumen that can receive a guiding element so that the system can be routed to the desired location. The catheter further is provided with lumens in communication with the housing. There is a cutout or window in the housing which is positioned in a vessel or interstitial space at the area where material is to be removed. The housing is further configured with an element that excises an atheroma or ablates the tissue of a gland and which can be caused to move into and out of the window by an actuating element and which can be caused to reciprocate to supply a cutting action by a driving element. The actuating element and the driving element both extend out to the exterior or proximal end of the system where each can be accessed and operated by a physician.

In one aspect of the invention, the catheter of the invention is cylindrically-shaped, and the housing has the contours of an ellipse, to approximate the surface of the vessel in which the atherectomy is to be performed. A balloon is provided at the distal end of the system at a location that is approximately opposite the cutout, so that by inflating the balloon the cutout will be pressed or pushed up against the treatment site.

In another aspect, the excising or ablating element can be connected to the actuator element and to the housing with a rivet and slot combination which is such that, when the actuator is pushed distally along the longitudinal axis of the housing, the excising or ablating element slowly closes the window and seals off from the interior of the housing the surrounding environment of the vessel as it excises or ablates the target material.

In a presently preferred embodiment, the excising or ablating element comprises two blades, each having a length approximating the length of the cutout measured along the longitudinal access of the housing having a combined width that allows the blades to be positioned across the cutout to effectively close off the window to the environment exterior to the housing.

In a different embodiment, the excising or ablating element comprises a single blade having a length approximating the length of the cutout and a width such that it can be positioned across the window to close it off.

In another aspect, the catheter system further is provided with an element for collecting resected material. This collection element can be configured either to retain the debris elsewhere in the housing until the system is withdrawn or to remove the material out through a lumen in the catheter during the procedure. In addition, an imaging element can be provided to aid in optimally positioning the window to result in a cut of the desired depth.

To use the system in an atherectomy, the catheter bearing the housing is positioned in the vessel of interest by means of the guiding element and is advanced until the window is positioned at the site at which treatment is to be rendered. The balloon is inflated to push the open window against the plaque, and the driving element is activated to start reciprocation of the blades back and forth along the longitudinal slot provided in each blade. At this point, the physician may rely on any ultrasonic imaging element that is provided on the actuator to assess the depth of the atheroma. The actuator then slowly is pushed longitudinally through the housing towards the distal end of the catheter system. The slots in the actuator are diagonally oriented such that when the actuator moves forward, the rivet connecting the blades and the actuator slides in towards the center of the housing. This action causes the blades to move within the contour of the housing and into the window, the blades reciprocating as they move. Thus, the blades resect the unwanted tissue while slowly closing off the window to the outside environment. Once the window is closed off, the driving element is deactivated and, if a collection element is provided, it can be used to push the cut tissue into the nose of the housing or to pull the debris outside the patient by vacuum or other suctioning means.

Adapting the system for use in prostatectomies can be accomplished by providing a separate heating element or by configuring an existing element, such as the blade or blades, to have variable temperature.

The system of the invention can be positioned without open surgery and allows for efficient removal of atheromas by providing a sharp, generally straight cutting edge or edges in a catheter and housing combination that nevertheless is flexible enough to negotiate the tortuous vessels of a patient. Importantly, the cutting operation of the invention results in a smooth and even luminal surface after treatment that approximates the luminal surface of a healthy section of a blood vessel. If the system is used in a prostectomy, less time-consuming manipulation is required to insure that the cutting operation will not remove material that is not intended to be removed than are prior art of prostectomy systems. When a guiding element disposed in a dedicated guide lumen is provided, a procedure using the system of the invention is further efficient in terms of time because, once the guiding element is in place, no extension wire or other apparatus is a prerequisite to insertion or removal of the catheter and housing. Regardless of the nature of the guiding element, the procedure also is efficient in terms of labor, because the infusion of the inflation medium and initiation of the reciprocation of the blade or blades, as well as any collection mechanism provided, can be configured to be operable via a foot pedal thus leaving the hands of a clinician free to simultaneously operate the various features of the system.

These and other advantages of the invention will become more apparent from the following detailed description thereof, when taken in conjunction with the accompanying exemplary drawings.

BRIEF DESCRIPTION OF THE DRAWINGS

FIG. 1 is a side elevational view of an atherectomy system incorporating the invention;

FIG. 2 is a perspective view of the excising or ablating element of the invention;

FIG. 3 is a perspective view of the housing of the invention, showing the span of the window;

FIG. 4 is an exploded, perspective view of the invention illustrating the connection between a blade, the actuator and the housing of the invention;

FIGS. 6A and 6B are perspective views of the invention showing the collection mechanism and imaging arrangement;

FIG. 7 is an exploded, perspective view of an alternate embodiment illustrating the connection between the single blade, the actuator and the housing of the invention;

FIGS. 8A–8E are perspective, progressive views of the embodiment of FIG. 7, as the actuator is advanced distally;

FIG. 9 is a side elevational view of an atherectomy system incorporating the invention with a heater for use in a prostectomy; and FIGS. 10A–10E schematically depict a method of using the invention.

DETAILED DESCRIPTION OF THE PREFERRED EMBODIMENT

Figure 5A:
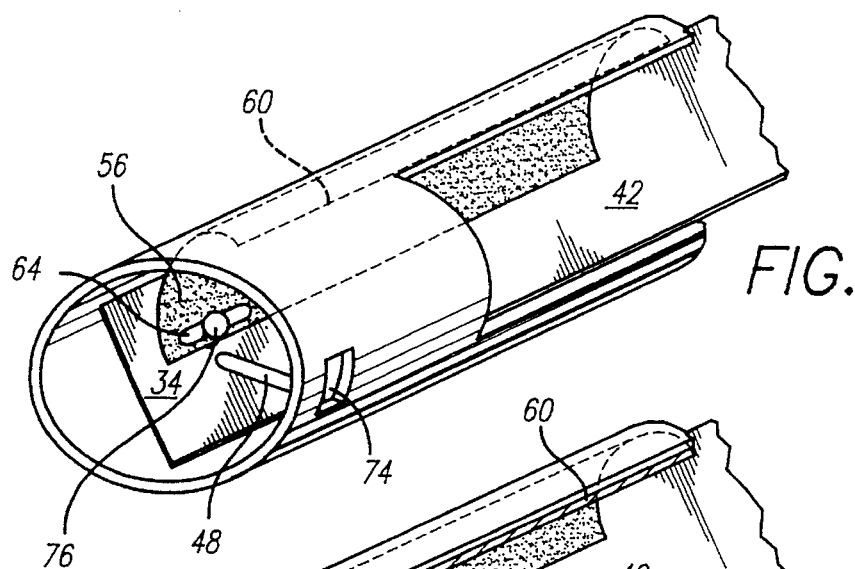
FIGS. 5A–5D are perspective, progressive views of the invention as the actuator is advanced distally.

Referring now to the drawings and, particularly, to FIGS. 1–4, there is illustrated a presently preferred embodiment of the invention. Catheter system 18 has distal end 20, housing 22, and catheter member 24. The catheter member is generally cylindrical in shape, and has lumens 26, 28, and 30, and inflatable member 32.

Lumen 26 extends from distal end 20 to the proximal end (not shown) of catheter element 24, which proximal end remains exterior to the body of the patient when an atherectomy procedure is being performed. This lumen is adapted to receive guiding member 27 which also extends to the exterior of the body of the patient during a procedure and which is used to manipulate and position system 18 at the site at which treatment is to be rendered.

Lumen 28 is in communication with inflatable member 32 and extends from a point where the inflatable member is attached to housing 22, just proximal to distal end 20, to the proximal end of catheter member 24 exterior to the body of the patient. The lumen is adapted to receive an inflation medium, such as a liquid or a gas, which will inflate the inflatable member. To insure that catheter member 24, including inflatable member, and housing 22 are both sufficiently rigid and sufficiently flexible for effective negotiation and deployment of system 18 in the blood vessels of a human patient, these elements are fabricated from a material such as polyamid-imide, nylon, polycarbonate, polyethylene, polyethylene terephythalate (manufactured under the trademark PET by the E.I. Dupont deNemours, Company), or any of the same reinforced with carbon fibers, glass fibers, or the like.

Lumen 30 is in communication with housing 22 and is adapted to receive actuator 34, excising or ablating element 36 and drive mechanism 80.

Housing 22 has proximal end 40, aperture or cutout 42, and nose 44 at distal end 20. The cutout or window is formed in the housing by injection molding or other suitable technique. The cross section of the housing is generally elliptical, so that the shape of the housing approximates the cross sectional shape of a typical blood vessel. When balloon 32 is inflated and the window is pressed up against a diseased area of a blood vessel, the profile of the window generally will follow the contours of what would be a healthy vessel wall. With this shape, after the cutting operation is performed, the cut or shaved section of the vessel is less likely to be uneven than would be the case if prior art devices were used, and the resultant uniform surface area will enhance the degree to which blood flow through the treated area is improved, since the treated area will have substantially the same contours as healthy areas proximal and distal to the treated area. The housing is attached to catheter member 24 by epoxy welding or other suitable method known to one of ordinary skill in the art. The window has length, $l_w$, and a width or span, $w_w$, corresponding to the arc defined by the radii of the portion of the ellipsoidal cross section of housing 22 that comprises the aperture. Side walls 68 and 70 of the housing have slots 72 and 74 which are circumferential or peripheral to follow the elliptical contour of the housing.

Actuator 34 is slidably disposed in housing 22 and extends from a point just proximal to nose 44 out to the proximal end of catheter system 18 and the exterior of the body of the patient. The actuator has slots 46 and 48 cut out near the distal end thereof. The distal end of each slot is oriented towards centerline, c, of the actuator and the slots extend diagonally such that the proximal end of slot 46 is oriented towards first edge 52 of the actuator and slot 48 is oriented to second edge 54 of the actuator. The slots are aligned so as to begin and end at the same lateral planes of the actuator.

Excising or ablating element 36 is comprised of cutters or blades 56 and 58, each of which is curved to approximate the generally elliptical contour of housing 22. Curved blade 56 has straight cutting edge 60 and longitudinal slot 64 disposed near the distal end thereof. Curved blade 58 has straight cutting edge 62 and longitudinal slot 66 disposed at approximately the same distance from the distal end of the blade as is slot 64 from the distal end of blade 56. Each excising or ablating element has a length, $l_b$, that is greater than length, $l_w$, of window 42. The blades have a combined length that completely covers span, $w_w$, of the window when the cutting edges of the blades are in contact, thus closing off window 42 to the environment exterior to the housing.

Rivet 76 connects excising or ablating element 56 and actuator 34 to housing side wall 68 through slots 64, 46 and 72. A similar connection is achieved by a rivet (not shown) between excising or ablating element 58 and actuator 34 to housing side wall 70 through slots 66, 48 and 74. This manner of connection allows the blades to reciprocate, i.e., to move back and forth along the length of the longitudinal slots, and to move into and out of window 42 to open and close it respectively. Specifically, when the actuator is pushed towards distal end 20, the rivets are forced towards edges 52 and 54 of the actuator and up towards the top end of peripheral slots 72 and 74, causing the blades to enter the window and eventually close it off. When the actuator is pulled away from the distal end, the rivets are forced towards centerline, c, of the actuator and down towards the bottom of the circumferential slots, therefore causing the blades to move out of the window and to rest against the sidewalls of the housing, leaving the window open.

Drive mechanism 80 is provided to cause the excising or ablating elements to reciprocate. The mechanism is comprised of cable 82 spirally disposed around drive wire 84, and is connected to a motor (not shown) outside the patient and to each blade of the excising or ablating element. The drive wire is manufactured from a material strong enough to initiate and maintain sufficient reciprocating action and flexible enough to allow negotiation of tortuous blood vessels without breakage. Suitable materials include stainless steel and nitinol. If stainless steel is used, a tarn of KEVLAR can be laid under the wire to minimize the degree to which the wire can stretch in a longitudinal direction. It has been determined that when the motor supplies the drive wire with a torquing force of approximately 750 revolutions per minute (RPMs), blades 56 and 58 reciprocate at an optimum rate for resecting plaque from the blood vessel.

Figure 5B:
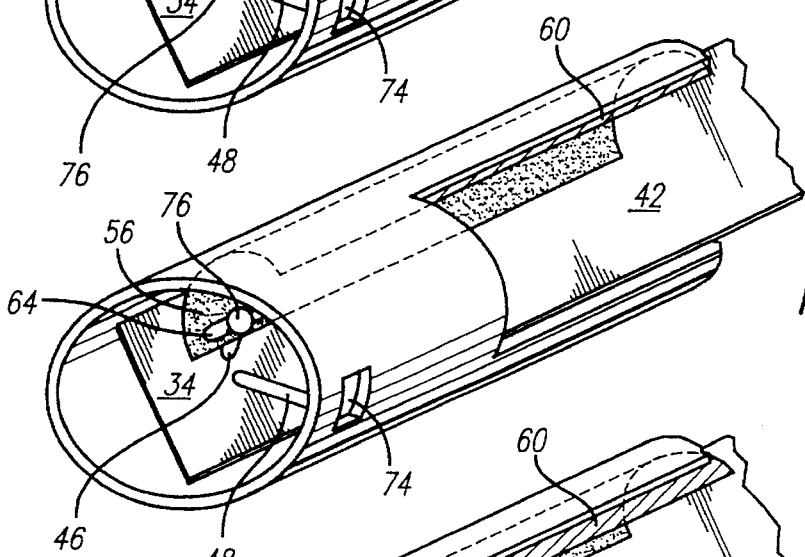
Figure 5C:
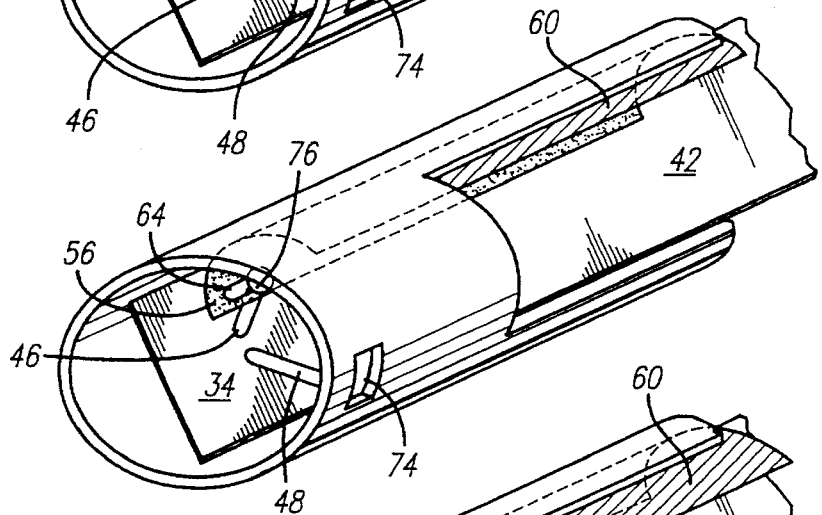
Figure 5D:
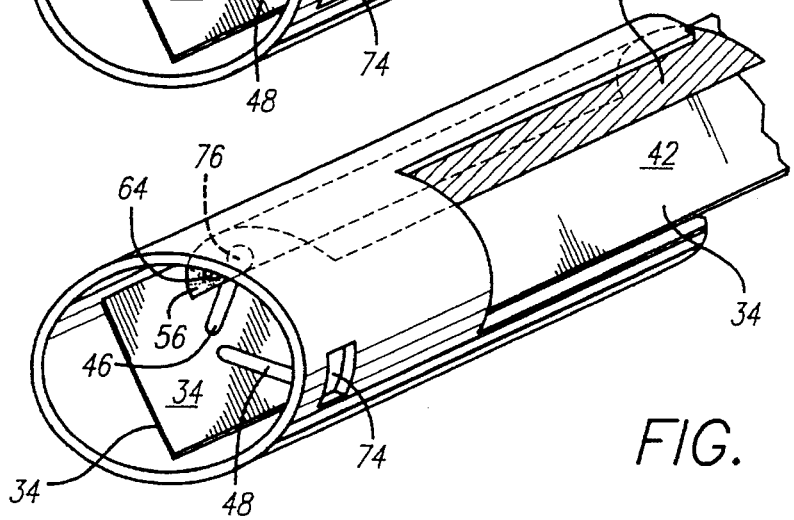

The progressive advancement of blade 56 into the window is illustrated in FIGS. 5A–5D. Blade 58 is not shown. The shaded areas in FIGS. 5A and 5B represent the inner surface of blade 56. The cross hatched areas in FIGS. 5B–5D represent the outer surface of blade 56. In FIG. 5A, the window is completely open and rivet 76 rests at the bottom of peripheral slot 72 and at the distal end of diagonal slot 46 of actuator 34. In FIG. 5B, actuator 34 has been advanced towards distal end 20, and the rivet has moved up along housing slot 72 and out towards actuator edge 52, causing cutting edge 60 to appear in window 42. At this point, drive mechanism 80 can be activated to start reciprocating the blades. In FIG. 5C, the actuator has been advanced further towards the distal end of the system, and more of the blade has entered window 42. Finally, in FIG. 5D, the actuator has been pushed as far as it can be, and the rivet is at the top of the housing slot and at the end of the diagonal slot closest to the outermost edge of the actuator. It can be appreciated that if blade 58 were illustrated, at FIG. 5D the window would be completely closed off.

Drive mechanism 80, inflation lumen 28 and plunger driver 96 all can be connected to a console exterior to the patient and selectively operated through a switching arrangement. The drive mechanism and plunger can be activated either by pushing buttons or by operating a foot pedal, as can the function of supplying the inflation medium to inflatable member 32 of catheter member 24.

As shown in FIGS. 6A and 6B, atherectomy catheter system 18 further can be provided with collection mechanism 90 which is disposed in housing 22, for pushing material cut from the blood vessel wall into nose 44 of the housing. The collection mechanism includes plunger 92, plunger actuator 94 and plunger driver 96, which can be a cable and wire arrangement similar to that used for blade drive mechanism 80. The plunger driver is connected to a motor (not shown) outside the patient. The motor can be activated to cause the plunger to reciprocate and the plunger actuator can be pushed to cause the plunger to traverse the length of window 42 every few seconds while an atherectomy is being performed. The housing nose has chamber 98 separated from the rest of the housing by screen 100. The screen comprises a fine mesh of wire or plastic. When the cut material is pushed against it by the force of the plunger, the material passes through the mesh into the chamber. The material will not pass back through the screen into the main body of the housing in the absence of an applied pushing force, and thus will remain in the chamber until the procedure is completed and the catheter system is removed from the patient.

As shown in FIG. 6A, atherectomy system 18 further is provided with ultrasonic imaging array 102, which is affixed to actuator 34 between and below blades 56 and 58. Array 102 is connected to ultrasonic imaging fibers 104 that extend outside the patient and which can be connected to a monitoring device. Using this imaging arrangement, each area to be treated can be located ultrasonically and then continually monitored to assess the change in the contour of the vessel wall as the atherectomy progresses.

Referring now to FIGS. 7 and 8, an alternate embodiment of the invention is illustrated. Catheter system 110 has only single cutter or blade 112. Blade 112 has longitudinal slot 114 to allow it to reciprocate as it traverses aperture or window 116. Actuator 118 has diagonal slot 120 which runs from one outer edge of the actuator to the other, to allow the blade enough range of movement to completely close off the window. The actuator and blade are connected to housing 122 through circumferential slot 124 by rivet 126. FIGS. 8A–8E illustrate the progressive advancement of blade 112 into the window. The shaded areas in FIGS. 8A and 8B represent the inner surface of the blade. The cross hatched area in FIGS. 8B–8E represent the outer surface of the blade. In FIG. 8A, the window is completely open and rivet 126 rests at the bottom of circumferential slot 124 and at the distal end of diagonal slot 120 of actuator 118. In FIG. 8B, actuator 118 has been advanced towards distal end 128 of catheter system 110, and the rivet has moved up along housing slot 124 and out towards actuator edge 130, causing cutting edge 134 to appear in window 116. At this point, drive mechanism 136 can be activated to start reciprocating the blade. In FIGS. 8C and 8D, the actuator has been advanced further towards the distal end of the system, and more of the blade has entered the window. Finally, in FIG. 8E, the actuator has been pushed as far as it can be, and the rivet is at the top of the housing slot and at the end of the diagonal slot closest to the outermost edge of the actuator.

To adapt the catheter system of either the preferred embodiment or the alternate embodiment for use in prostatectomies, the blades or blade are supplied with heater 140. As can be seen in FIG. 9, the heater can comprise a first electrical connection or lead 142 for attachment to blades 56 and 58 and a second electrical connection or lead 146 for heating attached to the blades at a position different from the point of connection of lead 142. Outside the body of the patient, the first and second leads are connected to a power source (not shown), which can be used to selectively raise the temperature of the blades.

As can be appreciated, various modifications can be made to the present invention without departing from the scope thereof. For example, alternate embodiments of the invention can include more than one balloon element, to allow for more accurate positioning of the window around and against the atheroma. The catheter can have a fixed guiding element to obviate the need for a separate guiding element lumen and to lower the profile of the overall system to allow access to smaller vessels or smaller interstitial spaces. Alternatively, the catheter can have a guiding element lumen that exits the body of the catheter part way down the member catheter shaft, allowing for the rapid exchange of the catheter and housing without disturbing the position of the guiding member. A fourth lumen can be provided in the catheter member which runs along the bottom of the housing to about the midpoint of the actuator, for routing ultrasonic imaging fibers to the imaging array or imaging crystals used to assess the depth of the plaque. Another alternative feature is a drive mechanism for the blades that is synchronized with the plunger driver. More specifically, the number of system elements can be reduced by connecting the plunger driver to the drive mechanism and setting the timing of the two operations of reciprocating the blades and collecting the debris such that plunger begins reciprocating when the blades are caused to stop reciprocating.

OPERATION OF THE SYSTEM

Referring now to FIG. 10, a method of using the preferred embodiment of the atherectomy system of the invention is as follows. Guidewire 27 is inserted through a percutaneous incision in a peripheral artery of a patient, such as the femoral or brachial artery. The guidewire is pushed and torqued distally through the vessels of the body until the tip of the guidewire is in vessel 152, the vessel to be treated, just proximal of atheroma 154. The location of the tip of the guidewire can be tracked or monitored by standard radiography techniques. Once the guidewire is in position, atherectomy system 18 is mounted over it and the system is advanced so that cutout 42 is at site 154. Detection of the contours of the site to be treated, such as the depth of the atheroma, can be assisted by ultrasonic imaging using linear crystal array 102 and ultrasonic imaging fibers 104. Blades 56 and 58 are retained against the inner walls of housing 22 during delivery of the window to the treatment site, by keeping actuator 34 in its most proximal position.

Outside the body, connections are made from the drive mechanism, plunger driver and inflation medium source to the control console. These connections can be made before or after the system has been fully advanced to the atheroma.

Referring now to FIG. 10B, after locating window 42 under atheroma 154, inflatable member 32 is inflated by supplying an inflation medium through lumen 28, thus pushing window 42 up under the atheroma. FIG. 10C illustrates the system after drive mechanism 80 is activated to start blades 56 and 58 reciprocating and actuator 34 has begun to be pushed towards distal end 20, such that the blades begin to close over the window and resect stenosed area 154 of vessel 152.

In FIG. 10D, window 42 is shown completely closed off by blades 56 and 58, the actuator having been pushed distally as far as diagonal slots 46 and 48 allow and drive mechanism 80 having been deactivated to stop reciprocation of the blades. The cut tissue is trapped under the blades. Inflatable member 32 then is deflated, and with the windows remaining closed, and system 10 is removed from the body of the patient. The surface of treated vessel 152 appears approximately as is shown in FIG. 10E.

In a prostectomy, the catheter system 18 is delivered to the prostate via a cystoscope inserted through the urethra. An incision in the prostatic urethra allows access to the tissue to be ablated. Once the window is positioned against the gland, reciprocation and heating of the blade or blades can be initiated. As the actuator is advanced the cutout is closed off and the ablation debris is trapped within the housing. The system is withdrawn through the cystoscope to conclude the procedure.

From the foregoing it is apparent that there is described and provided an improved atherectomy system and method for using such a system, which also is useful in prostectomy procedures. While the particular embodiments of the atherectomy system hereon disclosed are illustrative of a system that achieves the advantages of the invention, the embodiments are merely illustrative and not intended to limit the invention as it is otherwise defined in the claims.

What is claimed is:

1. A catheter system for excising material from a patient, the system comprising:

a flexible catheter member having a proximal end and a distal end, a housing disposed at said distal end, at least one treatment lumen in communication with said housing, and means for guiding said catheter member to the site at which treatment is to be rendered;

said housing having an aperture cut out therein and means for excising material disposed about said aperture, said excising means adapted to deliver a cutting action to cut the material situated within said aperture and further adapted to close off said aperture to the environment exterior to said housing, wherein said housing is provided with at least one slot disposed peripherally therein, said excising means is provided with at least one slot disposed along a longitudinal axis thereof and said actuating means is provided with at least one slot diagonally disposed thereon, and a rivet is provided to slidably connect together each said peripheral slot, each said longitudinal slot and each said diagonal slot.

2. The system of claim 1, wherein said housing further is provided with a conical portion at the most distal end thereof, said conical portion being located distally of said aperture and means for packing debris collected in said aperture into said conical portion, said packing means being disposed in one of said treatment lumens.

3. The system of any of claims 1 or 2, further comprising means for heating said excising means, said heating means being disposed in one of said treatment lumens.

4. An atherectomy system for insertion into a body lumen of a human patient, the atherectomy system comprising:

a flexible catheter member having a proximal end and a distal end, the catheter member having at least one lumen therein disposed along a longitudinal axis of the catheter member adapted for receiving a guiding member;

a housing disposed near the distal end of the flexible catheter member, the housing having a cutout therein, the cutout having a length and a width;

cutting means for resecting material from the body lumen, the cutting means being disposed within the housing and having at least one excising element, each of the excising elements having a length that is longer than the length of the cutout and a width at least as great as the width of the cutout;

drive means connected to the cutting means for causing the cutting means to reciprocate, and;

actuating means for advancing and withdrawing the cutting means for opening and closing the cutout, the actuator means attached by connecting means to the housing and to the cutting means, wherein the connecting means includes a longitudinal slot in each excising element of the cutting means, a diagonal slot corresponding to each excising element in the actuator means, a circumferential slot corresponding to each excising element in the housing, and a rivet connecting each excising element through the longitudinal slot, the diagonal slot and the circumferential slot to the housing and the actuating means.

5. An atherectomy system for insertion into a body lumen of a human patient, the atherectomy system comprising:

a flexible catheter member having a proximal end and a distal end, the catheter member having at least one lumen therein disposed along a longitudinal axis of the catheter member adapted for receiving a guiding member;

a housing disposed near the distal end of the flexible catheter member, the housing having a cutout therein, the cutout having a length and a width, wherein the housing has a first sidewall and a second sidewall;

cutting means for resecting material from the body lumen, the cutting means being disposed within the housing and having at least one excising element, each of the excising elements having a length that is longer than the length of the cutout and a width at least as great as the width of the cutout, the cutting means comprised of a first excising element and a second excising element, the first and second excising elements configured to follow the contours of the sidewalls of the housing, the first excising element further having a first straight cutting edge and the second excising element having a second straight cutting edge;

drive means connected to the cutting means for causing the cutting means to reciprocate, and;

actuating means for advancing and withdrawing the cutting means for opening and closing the cutout, the actuator means attached by connecting means to the housing and to the cutting means.

6. The atherectomy system of claim 5, wherein the housing has a generally elliptical cross section.

7. The atherectomy system of claim 5, wherein the connecting means includes a first longitudinal slot in the first excising element of the cutting means, a second longitudinal slot in the second excising element of the cutting means, a first diagonal slot in the actuating means and a second diagonal slot in the cutting means, a first circumferential slot in the first sidewall of the housing and a second circumferential slot in the second sidewall of the housing, a first rivet connecting the first excising element to the actuating means through the first longitudinal slot, the first diagonal slot and the first circumferential slot, and a second rivet connecting the second excising element to the actuator through the second longitudinal slot, the second diagonal slot and the second circumferential slot.

8. The atherectomy system of claim 7, wherein the flexible catheter member includes an inflatable member disposed near the distal end of the catheter member and an inflation lumen disposed within the catheter member and connected to the inflatable member and extending to the proximal end of the catheter member.

9. A catheter system for excising material from a patient, the system comprising:

a flexible catheter member having a proximal end and a distal end, a housing disposed at the distal end, at least one treatment lumen in communication with the housing, and means for guiding the catheter member to the treatment site;

the housing having an aperture cut out therein and means for excising material disposed about the aperture;

the excising means being disposed outside the housing and adapted to deliver a cutting action to cut material situated within the aperture and further adapted to close off the aperture to the environment exterior to the housing, wherein the excising means comprises at least one cutting blade having a cutting edge running parallel to the longitudinal axis of the housing.

10. A catheter system for excising material from a patient, the system comprising:

a flexible catheter member having a proximal end and a distal end, a housing disposed at the distal end, and at least one treatment lumen in communication with the housing;

the housing having an aperture cut out therein and an excising assembly for excising material disposed about the aperture, the excising assembly having two cutting blades, each cutting blade having a cutting edge passing generally longitudinally to the body of the catheter, the excising assembly being adapted to move the cutting edge of each blade across the longitudinal opening of the aperture in the housing in a direction perpendicular to the direction of the reciprocating cutting action, the cutting edges of each cutting blade moving in opposed lateral directions; and the cutting blades having a combined area larger than the area of the aperture, and wherein the opposing movement of the cutting edges across the longitudinal opening of the aperture positions the cutting blades over the aperture so as to close off the aperture to the environment exterior to the housing.

11. A catheter system for excising material from a patient, the system comprising:

a flexible catheter member having a proximal end and a distal end, a housing disposed at the distal end, and at least one treatment lumen in communication with the housing;

the housing having an aperture defining an area therein, and an excising assembly for excising material disposed about the aperture, the excising assembly having two cutting blades, each cutting blades having a cutting edge, the excising assembly being adapted to move the cutting edge of each blade in opposed lateral directions; and the cutting blades having a combined area larger than the area of the aperture, and wherein the opposing lateral movement of the cutting edges positions the cutting blades over the aperture so as to close off the aperture to the environment exterior of the housing.

* * * * *